United States Patent
Schmahl et al.

(10) Patent No.: US 9,282,798 B2
(45) Date of Patent: Mar. 15, 2016

(54) LIGHTENING PROCESS WITH BLONDING MOUSSE

(75) Inventors: Melanie Schmahl, Sisseln (CH); Frank Janssen, Cologne (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/234,758

(22) PCT Filed: May 29, 2012

(86) PCT No.: PCT/EP2012/060036
§ 371 (c)(1),
(2), (4) Date: Apr. 28, 2014

(87) PCT Pub. No.: WO2013/013862
PCT Pub. Date: Jan. 31, 2013

(65) Prior Publication Data
US 2014/0283866 A1  Sep. 25, 2014

(30) Foreign Application Priority Data
Jul. 27, 2011  (DE) .................. 10 2011 079 922

(51) Int. Cl.
| | | |
|---|---|---|
| *A61Q 5/08* | (2006.01) | |
| *A45D 7/04* | (2006.01) | |
| *A61K 8/41* | (2006.01) | |
| *A61K 8/44* | (2006.01) | |
| *A61K 8/04* | (2006.01) | |
| *A61K 8/22* | (2006.01) | |
| *A45D 7/00* | (2006.01) | |

(52) U.S. Cl.
CPC . *A45D 7/04* (2013.01); *A61K 8/046* (2013.01); *A61K 8/22* (2013.01); *A61K 8/41* (2013.01); *A61K 8/44* (2013.01); *A61Q 5/08* (2013.01); *A45D 2007/001* (2013.01); *A61K 2800/5922* (2013.01); *A61K 2800/882* (2013.01)

(58) Field of Classification Search
CPC ........... A61Q 5/08; A61K 8/046; A61K 8/44; A61K 8/41; A61K 8/22; A61K 2800/5922; A61K 2800/882; A45D 2007/001
USPC ........................ 8/111, 431; 132/202; 424/62
See application file for complete search history.

(56) References Cited

U.S. PATENT DOCUMENTS

| | | | |
|---|---|---|---|
| 6,540,791 B1 * | 4/2003 | Dias ................................. | 8/111 |
| 7,505,261 B2 | 3/2009 | Reasoner et al. | |
| 2004/0265258 A1 * | 12/2004 | Robinson et al. .......... | 424/70.12 |

FOREIGN PATENT DOCUMENTS

| | | |
|---|---|---|
| DE | 202009011154 U1 | 11/2009 |
| DE | 102009028523 A1 | 2/2011 |
| EP | 1237660 B1 | 8/2006 |
| EP | 2324811 A2 | 5/2011 |
| WO | 2005102539 A1 | 11/2005 |
| WO | 2007083206 A1 | 7/2007 |
| WO | 2007086730 A2 | 8/2007 |
| WO | 2007091882 A1 | 8/2007 |

OTHER PUBLICATIONS

STIC Search dated Oct. 1, 2014.*
PCT International Search Report (PCT/EP2012/060036) dated Sep. 23, 2014.
PCT Written Opinion (PCT/EP2012/060036) dated Sep. 23, 2014.

* cited by examiner

*Primary Examiner* — Eisa Elhilo
(74) *Attorney, Agent, or Firm* — P. Scott Smith

(57) ABSTRACT

Processes for lightening keratinic fibers are provided. In an exemplary process a ready-to-use lightening composition is produced by, immediately prior to application, combining a composition (A) comprising an alkalizing agent, a composition (B) comprising an oxidizing agent, and a composition (C) comprising a peroxo salt, and then mixing. The ready-to-use lightening composition is deployed from a foam dispensing vessel and distributed onto the fibers. The ready-to-use lightening composition is left on the fibers for a period of about 1 to about 60 min. and is washed out of the fibers.

16 Claims, No Drawings

LIGHTENING PROCESS WITH BLONDING MOUSSE

CROSS REFERENCE TO RELATED APPLICATIONS

The present disclosure is a U.S. National Stage entry under 35 U.S.C. §371 based on International Application No. PCT/EP2012/060036, filed May 29, 2012 which was published under PCT Article 21(2) and which claims priority to German Patent Application No. DE 10 2011 079 922.2 filed on Jul. 27, 2011, which is incorporated herein in its entirety by reference.

TECHNICAL FIELD

The invention relates to methods for lightening keratinic fibers, in which methods a ready-for-use agent is produced by blending 3 components and for the application is dispensed out of a foam dispensing vessel, as well as corresponding agents and kits of parts for lightening keratin-containing fibers.

BACKGROUND

Oxidative lightening agents are generally employed for lightening keratin-containing fibers. The comprised oxidizing agents, mostly at least hydrogen peroxide, act in this regard to destroy natural melanin dyes as well as synthetic dyes, when present in and on the keratinic fiber, thereby decolorizing the fiber. In order to lighten dark starting fibers the use of further oxidizing agents, especially per salts, such as per sulfates, is usually necessary.

In order to accelerate the reaction during the oxidative application, oxidative dyes mostly exhibit an alkaline pH value that is adjusted with alkalizing agents, such as alkanolamines, ammonia or inorganic bases. Although in this regard ammonia in particular affords good dyeing results, it also manifests disadvantages for the user due to its odor and irritation potential for skin and mucous membranes. Consequently, increased efforts have been made to develop efficient oxidative dyes that dispense with the use of ammonia.

Oxidative lightening agents usually consist of two or more components, whose mixture is sufficiently viscous to allow it to be comfortably applied onto hair without any dripping or running. In the case where per salts are used, these components are expediently in powder form. However, this brings additional challenges to such lightening agents. In particular, the production of the ready-for-use agents by blending powdered blonding salt components and often highly viscous, creamy or pasty alkalizer preparations and developer preparations is often laborious and laden with problems of uniform, intimate mixing. Therefore, in particular the agent has to be able to be easily and quickly mixable and easily applied so as to prevent inhomogeneities in the concentration of the ingredients during the application and thus to ensure a uniform and the least possible damaging lightening result.

Accordingly, at least one object of the present invention is to optimize methods with oxidative lightening agents, such that the abovementioned disadvantages can be overcome. In particular, it is intended to provide stable lightening agents free of unpleasant odors and which, if possible, should also be free of ammonia.

A known application form in the oxidative hair dye sector is the foam application that the consumer associates with uniform coloration results that are gentle to the hair fiber. However, a disadvantage of the foam application is the use of propellant gases typically employed to form the foam, because the ability to avoid the use of propellant gases has recently become more important.

Another problem associated with foam application is the stabilization of the foam. The consistency of foams is considered to be ideal when the dispensed product affords a solid, stable foam that leaves a supple feel and breaks down only slowly on the hair. It is frequently observed, however, that the applied foams possess little stability and rapidly collapse, leaving behind a low viscosity solution that drips. Having said that, it is also important that the foam nevertheless wets the hair well, so as enable a good lightening. The foam stability is negatively influenced in particular by the presence of larger amounts of salts.

Accordingly, another object of the present invention is furthermore to optimize methods for the use of oxidative lightening agents for the foam application without the use of propellant gases, such that the above cited disadvantages can be overcome. In addition, other objects, desirable features and characteristics will become apparent from the subsequent summary and detailed description, and the appended claims, taken in conjunction with the accompanying drawings and this background.

SUMMARY

It was surprisingly found that oxidative lightening agents in the form of stable foams can be very easily produced and applied by the consumer and moreover lead to improved lightening results.

A first subject matter of the present invention is therefore a method for lightening keratinic fibers comprising the steps:
  i. preparing the ready for use lightening agent immediately before use by combining
      an agent (A), comprising at least one alkalizer,
      an agent (B), comprising an oxidizing agent, and
      an agent (C), comprising at least one peroxo salt,
      and subsequently blending,
  ii. dispensing the ready for use lightening agent out of a foam dispenser and spreading the ready for use agent onto the fibers,
  iii. maintaining the lightening agent on the fibers for a period of 1 to 60 minutes, and
  iv. washing the remaining lightening agent out of the fibers.

DETAILED DESCRIPTION

Keratin-containing fibers are understood to mean wool, furs, feathers and particularly human hair. However, the dyes according to the invention can, in principle, also be used for dyeing other natural fibers, such as e.g. cotton, jute, sisal, linen or silk, modified natural fibers, such as e.g. cellulose regenerate, nitrocellulose, alkyl cellulose or hydroxyalkyl cellulose or acetyl cellulose.

The ready for use lightening agents according to the invention comprise the active substances in a cosmetically acceptable carrier. This cosmetic carrier is preferably aqueous, alcoholic or aqueous-alcoholic. In the context of the invention, an aqueous carrier comprises at least 40 wt %, especially at least 50 wt % water. For the purposes of the present invention, aqueous-alcoholic carriers are understood to mean water-containing compositions, comprising about 3 to about 70 wt % of a $C_1$-$C_4$ alcohol, in particular, ethanol or isopropanol. The agents according to the invention can additionally comprise further organic solvents, such as for example 4-methoxybutanol, ethyl diglycol, 1,2-propylene glycol, n-propanol, n-butanol, n-butylene glycol, glycerin, diethylene glycol monoethyl ether, and diethylene glycol mono-n-butyl ether, in so far as the foam formation and foam stability are not excessively negatively influenced. Preference here is given to all water-soluble organic solvents. Preferred inventive agents are characterized in that they additionally comprise a non-aqueous solvent, wherein preferred inventive agents comprise the solvent in a concentration of about 0.1 to about 30 wt %, preferably in a concentration of about 1 to about 20 wt %, quite particularly preferably in a concentration of about 2 to about 10 wt %, each relative to the agent.

The agent (A) comprises an alkalizer as the first component that is essential for the invention. The alkalizers that can be used are typically selected from inorganic salts, especially from the alkali metals and alkaline earth metals, organic alkalizers, especially amines, basic amino acids and alkanolamines, and ammonia.

The inventive inorganic alkalizers are preferably selected from the group consisting of sodium hydroxide, potassium hydroxide, calcium hydroxide, barium hydroxide, sodium phosphate, potassium phosphate, sodium silicate, potassium silicate, sodium carbonate and potassium carbonate. In the context of the invention, the basic amino acids that can be employed as an inventive alkalizer are preferably selected from the group consisting of L-arginine, D-arginine, D,L-arginine, L-lysine, D-lysine, D,L-lysine, particularly preferably L-arginine, D-arginine, D,L-arginine. Finally, ammonia is another preferred alkalizer. The additional alkalizers are preferably comprised in amounts of about 0.05 to about 10 wt %, particularly about 0.5 to about 5 wt %, each relative to the total weight of the ready-for-use agent.

In a particularly preferred embodiment, the agents according to the invention are formulated to be free of ammonia as the alkalizer. In this regard, "free of ammonia" according to the invention means that the ammonia content of the inventive agent is less than about 1 wt %, preferably less than about 0.5 wt %, in particular less than about 0.1 wt %, each relative to the ready-for-use agent.

It was found that especially the use of at least one alkanolamine as the alkalizer had a positive effect on the lightening power of the agent and in particular allowed ammonia to be dispensed with.

In a preferred embodiment of the first subject matter of the invention, the agent (A) comprises at least one alkanolamine as the alkalizer.

Inventively useable alkanolamines are preferably selected from alkanolamines from primary, secondary or tertiary amines containing a $C_2$-$C_6$ alkyl parent substance that carries at least one hydroxyl group. Particularly preferred alkanolamines are selected from the group consisting of 2-aminoethan-1-ol (monoethanolamine), 3-aminopropan-1-ol, 4-aminobutan-1-ol, 5-aminopentan-1-ol, 1-aminopropan-2-ol (monoisopropanolamine), 1-aminobutan-2-ol, 1-aminopentan-2-ol, 1-aminopentan-3-ol, 1-aminopentan-4-ol, 2-amino-2-methyl-propanol, 2-amino-2-methylbutanol, 3-amino-2-methylpropan-1-ol, 1-amino-2-methylpropan-2-ol, 3-aminopropane-1,2-diol, 2-amino-2-methylpropane-1,3-diol, 2-amino-2-ethyl-1,3-propane diol, N,N-dimethylethanolamine, methylglucamine, triethanolamine, diethanolamine and triisopropanolamine. Inventively quite particularly preferred alkanolamines are selected from the group 2-aminoethan-1-ol (monoethanolamine), 2-amino-2-methylpropan-1-ol, 2-amino-2-methyl-propane-1,3-diol and triethanolamine. Particularly preferred agents (A) comprise at least monoethanolamine as the alkanolamine.

The alkanolamines are preferably comprised in an amount of about 0.05 to about 20 wt %, particularly about 0.5 to about 15 wt %, each based on the total weight of the ready-for-use lightening agent.

However, it has been shown in extensive tests that precisely the strongly alkaline lightening preparations pose particular challenges to the foam-forming surfactant. In particular, foaming lightening agents with high amounts of fatty acid amidoalkyl betaines as the foam-forming surfactant, tend, particularly in the presence of alkanolamines as the alkalizing agent, to develop amine-like odors, which are perceived by the user as disturbing and unpleasant.

This unwanted side effect could be completely suppressed by choosing certain betaine-type surfactants.

One embodiment of the first subject matter of the invention is accordingly a method that is characterized in that the agent (A) additionally comprises a zwitterionic surfactant of the Formula (I),

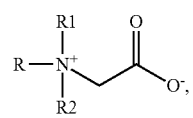

(I)

in which

R stands for a saturated or unsaturated $C_{10}$-$C_{20}$ alkyl chain and

R1 and R2 each stand independently of one another for a $C_1$-$C_4$ alkyl group or a $C_2$-$C_4$ hydroxyalkyl group.

The R group stands here for an alkyl chain containing 10 to 20, preferably 10 to 18 carbon atoms and can possess one or more double bonds and can be optionally branched. Preferred examples of such alkyl groups are the decyl, lauryl, myristyl, cetyl, palmoleyl, 2-hexyldecyl, stearyl, isostearyl, oleyl, elaidyl, petroselinyl, arachyl, 2-octyldodecyl or gadoleyl group as well as their mixtures, as would result from the employed raw material or production method. Alkyl groups based on cocoalkyl groups or tallow fat alkyl groups are preferred for R.

The R1 and R2 groups stand independently of one another for a $C_1$-$C_4$ alkyl group or a $C_2$-$C_4$ hydroxyalkyl group In this regard, suitable and preferred $C_1$-$C_4$ alkyl groups are the methyl, ethyl, propyl, isopropyl, butyl, 1-methylpropyl, 2-methylpropyl and 1,1-dimethylethyl groups. In this regard, suitable and preferred $C_2$-$C_4$ hydroxyalkyl groups are the 2-hydroxyethyl, 3-hydroxypropyl and 2-hydroxypropyl groups. Particularly preferably, R1 and R2 each stand for a methyl group.

One embodiment of the first subject matter of the invention is characterized in that the agent (A) comprises a compound of the Formula (I) as the zwitterionic surfactant, wherein R1 and R2 each stand for a methyl group and R for a cocoalkyl group.

Such particularly suitable zwitterionic surfactants have the INCI name Coco Betaine and are sold for example under the trade name Genagen® KB as an aqueous solution containing 30 wt % active substance.

In order to generate a stable foam, the ready-for-use agent needs to comprise a sufficient amount of zwitterionic surfactant. Accordingly, one embodiment of the first subject matter of the invention is characterized in that the agent (A) comprises one or more zwitterionic surfactants of the Formula (I) in a total weight fraction of at least 2.5 wt %, preferably at least 3 wt % and in particular at least 4 wt %, based on the total weight of the ready-for-use lightening agent.

In order to further improve the foam formation and foam stability, it can be inventively preferred to add additional, in particular non-ionic, surfactants to the lightening agent.

Therefore, another embodiment of the first subject matter of the invention is characterized in that the agent (A) additionally comprises a non-ionic surfactant, selected from alkyl polyglucosides and/or alkenyl polyglucosides and/or ethoxylated non-ionic surfactants containing at least 30 ethylene oxide units.

Alkyl polyglycosides as well as alkylene oxide addition products to saturated, linear fatty alcohols, fatty acid esters and fatty acids, each with 30 to 80 moles ethylene oxide per mole fatty alcohol or fatty acid, have proved to be preferred non-ionic surfactants. Ready for use preparations with excellent properties are also obtained when they comprise fatty acid esters of ethoxylated glycerine as the non-ionic surfactants.

According to a preferred embodiment, the agent (A) comprises an alkyl and/or alkenyl polyglucoside as the non-ionic surfactant. Known non-ionic surfactants of Formula (II) represent alk(en)yl polyglucosides,

in which $R^1$ stands for an alkyl or alkenyl group containing 4 to 22 carbon atoms, G for a sugar residue containing 5 or 6 carbon atoms and p for numbers from 1 to 10.

The alkyl and alkenyl polyglucosides can derive from aldoses or ketoses containing 5 or 6 carbon atoms, preferably from glucose. The preferred alkyl and/or alkenyl polyglucosides are therefore alkyl and/or alkenyl polyglucosides. The index value p in the general Formula (II) represents the degree of polymerization (DP), i.e. the distribution of mono and polyglucosides, and stands for a number between 1 and 10. Whereas in a given compound, p must always be a whole number and here above all can assume the values p=1 to 6, the value p for a specific alkyl oligoglucoside is an analytically determined calculated quantity that mostly represents a fractional number. Preferably, alkyl and/or alkenyl polyglucosides are employed with an average degree of oligomerization p of 1.1 to 3.0. From the industrial point of view, such alkyl and/or alkenyl polyglucosides are preferred with degrees of polymerization less than 1.7 and in particular between 1.2 and 1.4.

The alkyl or alkenyl group $R^1$ may be derived from primary alcohols containing 4 to 11 and preferably 8 to 10 carbon atoms. Typical examples are butanols, caproyl alcohol, caprylic alcohol, capric alcohol and undecyl alcohol as well as their industrial mixtures, such as for example those obtained by the hydrogenation of industrial fatty acid methyl esters or in the course of the hydrogenation of aldehydes from the Roelen Oxo-synthesis. Alkyl polyglucosides with chain lengths $C_8$-$C_{10}$ (DP=1 to 3) are preferred, which result as the low boiling fraction in the fractional distillation of industrial $C_8$-$C_{18}$ coco fatty alcohol and which can be contaminated with a fraction of less than 6 wt % of $C_{12}$ alcohol, as well as alkyl polyglucosides based on industrial $C_{9/11}$ oxo alcohols (DP=1 to 3). The alkyl or alkenyl group $R^1$ can moreover be derived from primary alcohols containing 12 to 22, preferably 12 to 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol as well as their industrial mixtures that can be obtained as described above.

Alkyl polyglucosides based on hydrogenated $C_{12}/C_{14}$ coco alcohol with a DP of 1 to 3 are preferred.

Inventively suitable alkyl and/or alkenyl polyglucosides are commercialized under the INCI name Coco-Glucoside and the trade name Plantacare 818 UP or under the INCI name Lauryl-Glucoside and the trade name Plantacare 1200 UP.

The alkyl or alkenyl polyglucosides are preferably comprised in the agents (A) according to the invention in amounts of about 0.1 to about 20 wt %, based on the ready-for-use lightening agent. Quantities of about 0.1 to about 15 wt % are particularly preferred. Quantities of about 3 to about 8 wt % are quite particularly preferred.

Moreover, it has proven advantageous if the agents (A) according to the invention comprise instead of or together with the alk(en)yl polyglucosides a non-ionic surfactant, ethoxylated, non-ionic surfactants with at least 30 ethylene oxide units.

Accordingly, another embodiment of the first subject matter of the invention is wherein the agent additionally comprises an ethoxylated surfactant containing at least 30 ethylene oxide units as the non-ionic surfactant.

Besides the correspondingly ethoxylated fatty alcohols, the addition products of 30 to 60 mol ethylene oxide on castor oil and hydrogenated castor oil are especially inventively particularly suitable. These specific non-ionic surfactants afford an additional improvement in the foam consistency, in particular with regard to a higher strength, an enhanced fine cell structure and a higher suppleness.

Examples of such suitable surfactants bear the INCI names Steareth-30, Ceteareth-30, Oleth-30, Ceteareth-50 or PEG-40 Hydrogenated Castor Oil and PEG-60 Hydrogenated Castor Oil. PEG-60 Hydrogenated Castor Oil is commercialized for example under the trade name Cremophor CO 60.

The ethoxylated, non-ionic surfactants are preferably comprised in the agents (A) according to the invention in amounts of about 0.1 to about 10 wt %, preferably from about 0.5 to about 8 wt % and particularly preferably from about 1.0 to about 5.0 wt %, each relative to the ready-for-use lightening agent.

According to the inventive method of the first subject matter of the invention, the agent (B) comprises an oxidizing agent. Oxidizing agents that come under consideration are per salts, peroxycarboxylic acids, chlorites and in particular hydrogen peroxide or its addition products on urea, melamine as well as sodium borate.

In a preferred embodiment of the first subject matter of the invention, the oxidizing agent of the agent (B) is hydrogen peroxide.

The oxidizing agent is preferably comprised in the agent (B) according to the invention in an amount of about 0.1 to about 10 wt %, preferably from about 0.5 to about 8 wt % and particularly preferably from about 1.0 to about 5.0 wt %, each relative to the ready-for-use lightening agent.

The addition of so-called complexants is also inventively preferred in the agent (B). Complexants are substances that can complex metal ions. In this way the metal catalyzed decomposition of hydrogen peroxide is reduced and thus the storage stability of the agent (B) is increased. Preferred complexants are so-called chelating complexants. Suitable and—in the context of the present invention—preferred chelating agents are, for example polyoxycarboxylic acids, polyamines, ethylenediaminetetraacetic acid (EDTA), ethylenediaminedisuccinic acid (EDDS), nitrilotriacetic acid (NTA) and hydroxyethane diphosphonic acids and their alkali metal salts. Inventively preferred complexants are phosphonates, preferably hydroxyalkane or aminoalkane phosphonates and especially 1,1-hydroxyethane-1,1-diphosphonate (HEDP) or its di- or tetrasodium salt and/or ethylenediaminetetramethylene phosphonate (EDTMP) or its hexasodium salt and/or diethylenetriaminepentamethylene phosphonate (DTPMP) or its hepta or octasodium salt. Dipicolinic acid is also inventively preferably used as a complexant. Agents that comprise a combination of an EDTA salt and HEDP and dipicolinic acid are inventively particularly preferred.

Complexants are preferably comprised in the agent (B) according to the invention in an amount of about 0.005 to about 1.5 wt %, preferably from about 0.01 to about 1 wt % and particularly preferably from about 0.05 to about 0.5 wt %, each relative to the ready-for-use lightening agent.

The agent (C) of the inventive method comprises at least one peroxo salt.

Preferred peroxo salts are peroxodisulfate salts, especially ammonium peroxodisulfate, potassium peroxodisulfate and sodium peroxodisulfate. The ready-for-use agent can preferably comprise the peroxodisulfate salts in an amount of about 0.1 to about 25 wt %, particularly in an amount of about 0.5 to about 15 wt %, based on the total weight of the ready-for-use lightening agent.

It has turned out that for a homogenous, uniform application, the peroxo salt should be characterized by a good mixability and a rapid dissolution as the agents (A), (B) and (C) are being blended. Moreover, this enables the agent to be dispensed in an improved manner out of the foam dispensing vessel in the second process step ii of the inventive method.

It was observed that especially sodium persulfate (=sodium peroxosulfate) and ammonium persulfate (ammonium peroxosulfate) are particularly suitable in this regard.

Consequently, in one embodiment of the first subject matter of the invention, the agent (C) is characterized in that it comprises sodium persulfate and/or ammonium persulfate as the peroxo salt.

The agent (C) can comprise additional components. Especially when packaging in powder form, it can be preferred to add additional thickeners, such as cellulose, cellulose derivatives, Xanthane or acrylic acid polymers, dedusting agents, such as mineral oils, or additional blonding activators, such as carbonates or silica, to the agent (C).

In the first step of the inventive method the agents (A), (B) and (C) are blended by combining the agents in a suitable vessel. In this regard, it has proven advantageous to carry out the blending directly in the foam dispensing vessel of the second process step.

Depending on the requirements of the consumer, the ready-for-use lightening agent could comprise additional ingredients that would be comprised either in one or in more of the agents (A), (B) and (C).

Furthermore, in the work on which this invention is based, it was found that it is advantageous if the ready-for-use lightening agents comprise an anionic surfactant in addition to the above cited surfactants. Inventively particularly preferred anionic surfactants are linear and branched fatty acids with 8 to 30 carbon atoms (soaps),
ether carboxylic acids of the formula R—O—($CH_2$—$CH_2O)_x$—$CH_2$—COOH, in which R is a linear alkyl group with 8 to 30 carbon atoms and x=0 or 1 to 16, and
alkyl sulfates and alkyl polyglycol ether sulfates of the Formula R—(O—$CH_2$—$CH_2)_x$—$OSO_3H$, in which R is preferably a linear alkyl group with 8 to 30 carbon atoms and x=0 or 1 to 12.

In a quite particularly preferred embodiment of the present invention, the ready-for-use lightening agents additionally comprise an anionic surfactant in addition to the surfactants that are essential for the invention. It has proven advantageous if the anionic surfactant is comprised in the oxidizing agent preparation (agent (B)) and the other surfactants are comprised in the agent (A).

Furthermore, in order to achieve the desired foam properties, it has proven to be inventively significant for the ready-for-use lightening agent, blended from the three agents (A), (B) and (C), to have a total surfactant content of at least about 10 wt %. Agents that contain at least about 11 wt %, preferably at least about 12 wt % total surfactant content, each relative to the ready-for-use lightening agent, are particularly preferred.

Moreover, it has proven to be advantageous if the ready-for-use preparation is formulated to be free of cationic surfactants.

For nuancing the resulting lightened tones it can be inventively preferred if the ready-for-use lightening agent additionally comprises a substantive dye. These are dye molecules that are directly absorbed onto the substrate and do not require any oxidative process to develop the color. The substantive dyes are each preferably employed in quantities of about 0.001 to about 20 wt %, based on the total end-use preparation.

Preferred anionic substantive dyestuffs are known compounds with the international designations or trade names Acid Yellow 1, Acid Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52 as well as Tetrabromophenol blue and Bromophenol blue.

Preferred cationic substantive dyes are here cationic triphenylmethane dyes, such as for example Basic Blue 7, Basic Blue 26, Basic Violet 2 and Basic Violet 14, aromatic systems that are substituted with a quaternary nitrogen group, such as for example Basic Yellow 57, Basic Red 76, Basic Blue 99, Basic Brown 16 and Basic Brown 17, as well as substantive dyes that comprise a heterocycle that exhibits at least one quaternary nitrogen atom. The compounds, which are also known under the names Basic Yellow 87, Basic Orange 31 and Basic Red 51, are quite particularly preferred cationic substantive dyes.

The cationic substantive dyes that are commercialized under the trade name Arianor® are likewise quite particularly preferred cationic substantive dyes according to the invention.

Preferred non-ionic substantive dyes are the known compounds with the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]-benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol.

It is not required that each of the substantive dyestuffs be pure compounds. In fact, due to the manufacturing processes for the individual dyes, minor quantities of even more components may be comprised, in so far as they have no detrimental influence on the coloration result or that they must be excluded on other grounds, e.g. toxicological.

In addition, naturally occurring dyestuffs may also be added, as are comprised for example in henna red, henna neutral, henna black, camomile leaves, sandalwood, black tea, alder buckthorn bark, sage, logwood, madder root, cachou and alkanet root.

It is also possible, in addition to the lightening, to achieve an oxidative coloration of the keratinic fibers if the ready-for-use lightening agent additionally comprises an oxidation dye precursor. In this case, for reasons of storage stability, the oxidation dye precursors are preferably made up in the agent (A). Oxidation dye precursors form their coloration from a developer component and optionally from a coupler component.

Preferred developer components are selected from at least one compound from the group consisting of p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-2-propanol, bis-(2-hydroxy-5-aminophenyl)methane, 1,3-bis-(2,5-diaminophenoxy)-2-propanol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxy-ethyl)phenol and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, as well as the physiologically acceptable salts of these compounds.

The developer components are preferably used in an amount of about 0.005 to about 20 wt %, preferably about 0.1 to about 5 wt %, in each case based on the ready-for-use lightening agent.

Inventively preferred coupler components are selected from 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2-hydroxyethyl)amino-2-methylphenol, 3-(diethylamino)phenol, N-cyclopentyl-3-aminophenol, 1,3-dihydroxy-5-(methylamino)benzene, 3-ethylamino-4-methylphenol, 2,4-dichloro-3-aminophenol, 2-(2,4-diaminophenoxy)ethanol, 1,3-bis-(2,4-diaminophenoxy)propane, 1-methoxy-2-amino-4-(2-hydroxyethylamino)benzene, 1,3-bis-(2,4-diaminophenyl)propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl) aminobenzene, resorcinol, resorcinol monomethyl ether, 2-methylresorcinol, 5-methylresorcinol, 2,5-dimethylresorcinol, 2-chlororesorcinol, 4-chlororesorcinol, pyrogallol, 1,2,4-trihydroxybenzene, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 2,6-dihydroxy-3,4-dimethylpyridine, 3,4-diaminopyridine, 2-(2-methoxyethyl)amino-3-amino-6-methoxypyridine, 2-(4'-methoxyphenyl)amino-3-aminopyridine, 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene, 2,3-dihydroxynaphthalene, 4-hydroxyindole, 6-hydroxyindole, 7-hydroxyindole, 4-hydroxyindoline, 6-hydroxyindoline, 7-hydroxyindoline, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine or mixtures of these compounds or their physiologically acceptable salts.

The coupler components are preferably used in an amount of about 0.005 to about 20 wt %, preferably about 0.1 to about 5 wt %, in each case based on the ready-for-use lightening agent.

Here, developer components and coupler components are generally used in approximately molar amounts relative to one another. Although the molar use has also proven to be expedient, a certain excess of individual oxidation dye precursors is not disadvantageous, meaning that developer components and coupler components may be present in a molar ratio of from about 1 to 0.5 to about 1 to 3, in particular, about 1 to 1 to about 1 to 2.

It was surprisingly found that the presence of small amounts of a polymeric thickener could have a positive influence on the foam stability. Accordingly, in the scope of an embodiment of the present invention, it is preferred if the ready-for-use lightening agents comprise a polymeric thickener.

Exemplary inventively preferred polymeric thickeners are: Acrylates Copolymer, Acrylamides Copolymer, Acrylamide/Sodium Acrylate Copolymer, Acrylamide/Sodium Acryloyldimethyltaurate Copolymer, Acrylates/Acetoacetoxyethyl Methacrylate Copolymer, Acrylates/Beheneth-25 Methacrylate Copolymer, Acrylates/C10-30 Alkyl Acrylate Crosspolymer, Acrylates/Ceteth-20 Itaconate Copolymer, Acrylates/Ceteth-20 Methacrylate Copolymer, Acrylates/Laureth-25 Methacrylate Copolymer, Acrylates/Palmeth-25 Acrylate Copolymer, Acrylates/Palmeth-25 Itaconate Copolymer, Acrylates/Steareth-50 Acrylate Copolymer, Acrylates/Steareth-20 Itaconate Copolymer, Acrylates/Steareth-20 Methacrylate Copolymer, Acrylates/Stearyl Methacrylate Copolymer, Acrylates/Vinyl Isodecanoate Crosspolymer, Acrylic Acid/Acrylonitrogens Copolymer, Agar, Agarose, Alcaligenes Polysaccharides, Algin, Alginic Acid, Ammonium Acrylates/Acrylonitrogens Copolymer, Ammonium Acrylates Copolymer, Ammonium Acryloyldimethyltaurate/Vinyl Formamide Copolymer, Ammonium Acryloyldimethyltaurate/VP Copolymer, Ammonium Alginate, Ammonium Polyacryloyldimethyl Taurate, Amylopectin, Ascorbyl Methylsilanol Pectinate, Astragalus Gummifer Gum, Attapulgite, Avena Sativa (Oat) Kernel Flour, Bentonite, Butoxy Chitosan, Caesalpinia Spinosa Gum, Calcium Alginate, Calcium Carboxymethyl Cellulose, Calcium Carra-geenan, Calcium Potassium Carbomer, Calcium Starch Octenylsuccinate, C20-40 Alkyl Stearate, Carbomer, Carboxybutyl Chitosan, Carboxymethyl Chitin, Carboxymethyl Chitosan, Carboxymethyl Dextran, Carboxymethyl Hydroxyethylcellulose, Carboxymethyl Hydroxypropyl Guar, Cellulose Acetate Propionate Carboxylate, Cellulose Gum, Ceratonia Siliqua Gum, Cetyl Hydroxyethylcellulose, Cholesterol/HDI/Pullulan Copolymer, Cholesteryl Hexyl Dicarbamate Pullulan, Cyam-opsis Tetragonoloba (Guar) Gum, Diglycol/CHDM/Isophthalates/SIP Copolymer, Dihydrogenated Tallow Benzylmonium Hectorite, Dimethicone Crosspolymer-2, Dimethicone Propyl PG-Betaine, DMAPA Acrylates/Acrylic Acid/Acrylonitrogens Copolymer, Ethylene/Sodium Acrylate Copolymer, Gelatin, Gellan Gum, Glyceryl Alginate, Glycine Soja (Soybean) Flour, Guar Hydroxypropyltrimonium Chloride, Hectorite, Hydrated Silica, Hydrogenated Potato Starch, Hydroxybutyl Methylcellulose, Hydroxyethyl Acrylate/Sodium Acryloyldimethyl Taurate Copolymer, Hydroxyethyl-cellulose, Hydroxyethyl Chitosan, Hydroxyethyl Ethylcellulose, Hydroxypropylcellulose, Hydroxypropyl Chitosan, Hydroxypropyl Ethylenediamine Carbomer, Hydroxypropyl Guar, Hydroxypropyl Methylcellulose, Hydroxypropyl Methylcellulose Stearoxy Ether, Hydroxypropyl Starch, Hydroxypropyl Starch Phosphate, Hydroxypropyl Xanthan Gum, Hydroxystearamide MEA, Isobutylene/Sodium Maleate Copolymer, Lithium Magnesium Silicate, Lithium Magnesium Sodium Silicate, Macrocystis Pyrifera (Kelp), Magnesium Alginate, Magnesium Aluminum Silicate, Magnesium Silicate, Magnesium Trisilicate, Methoxy PEG-22/Dodecyl Glycol Copolymer, Methylcellulose, Methyl Ethylcellulose, Methyl Hydroxyethylcellulose, Microcrystalline Cellulose, Montmorillonite, Moroccan Lava Clay, Natto Gum, Nonoxynyl Hydroxyethylcellulose, Octadecene/MA Copolymer, Pectin, PEG-800, PEG-Crosspolymer, PEG-150/Decyl Alcohol/SMDI Copolymer, PEG-175 Diiso-stearate, PEG-190 Distearate, PEG-15 Glyceryl Tristearate, PEG-140 Glyceryl Tristearate, PEG-240/HDI Copolymer Bis-Decyltetradeceth-20 Ether, PEG-100/IPDI Copolymer, PEG-180/Laureth-50/TMMG Copolymer, PEG-10/Lauryl Dimethicone Crosspolymer, PEG-15/Lauryl Dimethicone Crosspolymer, PEG-2M, PEG-5M, PEG-7M, PEG-9M, PEG-14M, PEG-20M, PEG-23M, PEG-25M, PEG-45M, PEG-65M, PEG-90M, PEG-115M, PEG-160M, PEG-120 Methyl Glucose Trioleate, PEG-180/Octoxynol-40/TMMG Copolymer, PEG-150 Pentaerythrityl Tetrastearate, PEG-4, Rapeseed amide, PEG-150/Stearyl Alcohol/SMDI Copolymer, Polyacrylate-3, Polyacrylic Acid, Polycyclopentadiene, Polyether-1, Polyethylene/Isopropyl Maleate/MA Copolyol, Polymethacrylic Acid, Polyquaternium-52, Polyvinyl Alcohol, Potassium Alginate, Potassium Aluminum Polyacrylate, Potassium Carbomer, Potassium Carrageenan, Potassium Polyacrylate, Potato Starch Modified, PPG-14 Laureth-60 Hexyl Dicarbamate, PPG-14 Laureth-60 Isophoryl Dicarbamate, PPG-14 Palmeth-60 Hexyl Dicarbamate, Propylene Glycol Alginate, PVP/Decene Copolymer, PVP Montmorillonite, Rhizobian Gum, Ricinoleic Acid/Adipic Acid/AEEA Copolymer, Sclerotium Gum, Sodium Acrylate/Acryloyldimethyl Taurate Copolymer, Sodium Acrylates/Acrolein Copolymer, Sodium Acrylates/Acrylonitrogens Copolymer, Sodium Acrylates Copolymer, Sodium Acrylates/Vinyl Isodecanoate Crosspolymer, Sodium Acrylate/Vinyl Alcohol Copolymer, Sodium Carbomer, Sodium Carboxymethyl Chitin, Sodium Carboxymethyl Dextran, Sodium Carboxymethyl Beta-Glucan, Sodium Carboxymethyl Starch, Sodium Carrageenan, Sodium Cellulose Sulfate, Sodium Cyclodextrin Sulfate, Sodium Hydroxypropyl Starch Phosphate, Sodium Isooctylene/MA Copolymer, Sodium Magnesium Fluorosilicate, Sodium Polyacrylate, Sodium Polyacrylate Starch, Sodium Polyacryloyldimethyl Taurate, Sodium Polymethacrylate, Sodium Polystyrene Sulfonate, Sodium Silicoaluminate, Sodium Starch Octenylsuccinate, Sodium Stearoxy PG-Hydroxyethylcellulose Sulfonate, Sodium Styrene/Acrylates Copolymer, Sodium Tauride Acrylates/Acrylic Acid/Acrylonitrogens Copolymer, Solanum Tuberosum (Potato) Starch, Starch/Acrylates/Acrylamide Copolymer, Starch Hydroxypropyltrimonium Chloride, Steareth-60 Cetyl Ether, Steareth-100/PEG-136/HDI Copolymer, Sterculia Urens Gum, Synthetic Fluorphlogopite, Tamarindus Indica Seed Gum, Tapioca Starch, TEA-Alginate, TEA-Carbomer, Triticum Vulgare (Wheat) Starch, Tromethamine Acrylates/Acrylonitrogens Copolymer, Tromethamine Magnesium Aluminum Silicate, Welan Gum, Xanthan Gum, Yeast Beta-Glucan, Yeast Polysaccharides, Zea Mays (Corn) Starch.

From this extensive group, the thickeners that comprise at least one monomer of the acrylic acid or methacrylic acid type as well as their derivatives, have proven to be particularly advantageous. An inventively quite particularly preferred polymer is the copolymer known under the INCI name Acrylates Copolymer of two or more monomers, selected from acrylic acid, methacrylic acid and their esters with $C_1$-$C_4$ alkyl groups.

It is particularly advantageous if the polymeric thickener is comprised in small amounts, preferably in amounts of about 0.05 to about 2.5 wt %, particularly about 0.3 to about 1.5 wt %, each based on the ready-for-use lightening agent.

A further improvement in the care properties of the products was achieved by incorporating an extract that is obtained from and/or with the aid of algae and/or plankton. In particular, the moisture balance of the fibers as well as their gloss could be considerably increased by these extracts. According to the invention, "extracts that are obtained from and/or with the aid of algae and/or plankton" are understood to mean mixtures of active substances that are obtained either by extraction of algae and/or plankton themselves or by extraction of the aqueous phase surrounding the algae and/or the plankton. Inventively preferred algae and/or plankton types are selected from the genera Haptophyta, Schlundgeissler (Cryptista), Euglenozoa, Dinozoa, Chlorarachniophyta, Gold algae (Chrysophyta), Silica algae (Bacillariophyta, also known as Diatomae), Brown algae (Phaeophyta), Dinogellatae, Red algae (Rhodophyta), Green algae (Chlorophyta), Picobiliphyta as well as Blue algae (for example Oscillatoria and Spirulina). In the context of the present invention, extracts from Blue algae occurring principally in fresh water are particularly preferred.

In regard to the ways and means of obtaining the inventive extracts from the algae and/or plankton ingredients, there are in principle no limitations. The extraction agent used to prepare the cited algae extracts can be water, alcohols as well as their mixtures. Exemplary preferred alcohols are lower alcohols such as ethanol and isopropanol, but particularly polyhydric alcohols such as ethylene glycol, propylene glycol and butylene glycol, both as the sole extraction agent as well as in aqueous mixtures. Blue algae extracts that have been obtained by means of a water/propylene glycol mixture have proven to be particularly suitable. In this regard, it has proven particularly suitable if these extraction agents are used in a ratio of about 1:10 to about 10:1.

Furthermore, it can be inventively preferred to incorporate extracts that have been at least partially decolorized prior to use. This can be carried out for example with active carbon. It is likewise possible to incorporate the aqueous breeding solution or culture solution of algae or plankton as the algae or plankton extract into the inventive agents. For this the algae or the plankton are firstly separated from the culture solution by means of a physical separation method, such as filtration or centrifugation.

In a particularly preferred embodiment of the present invention, the agent comprises an extract of a Blue alga, preferably a fresh water Blue alga, particularly preferably a Blue alga of the genus Spirulina.

The ready-for-use lightening agents according to the invention preferably comprise the algae extracts and/or the plankton extracts in an amount of about 0.001 to about 5 wt %, preferably about 0.01 to about 2 wt %, based on the ready-for-use agent.

In addition, it can be inventively preferred if the agents additionally comprise an amino acid and/or a protein. Inventively preferred amino acids are arginine, serine, lysine, glycine, tyrosine, proline, glutamine, cysteine and histidine. A surprisingly strong structuring of the hair is enabled by the amino acids and/or the proteins.

The inventors of the present applications have also shown that formulating the agents without silicone oils has an advantageous effect on the consistency of the foam.

Furthermore, the ready-for-use lightening agents according to the invention can comprise additional active substances, auxiliaries and additives, such as for example non-ionic polymers such as for example vinyl pyrrolidinone/vinyl acrylate copolymers, polyvinyl pyrrolidinone, vinyl pyrrolidinone/vinyl acetate copolymers, polyethylene glycols and polysiloxanes; additional silicones such as volatile, non-volatile, linear, branched or cyclic, crosslinked or uncrosslinked polyalkylsiloxanes (like dimethicone or cyclomethicone), polyarylsiloxanes and/or polyalkylarylsiloxanes, in particular polysiloxanes with organofunctional groups, such as substituted or unsubstituted amines (amodimethicone), carboxyl, alkoxy and/or hydroxyl groups (Dimethicone copolyols), linear polysiloxane(A)-polyoxyalkylene(B)-block copolymers, grafted silicone polymers; cationic polymers such as quaternized cellulose ethers, polysiloxanes with quaternary groups, dimethyldiallylammonium chloride polymers, acrylamide-dimethyldiallylammonium chloride copolymers, dimethylaminoethyl methacrylate-vinyl pyrrolidinone copolymers quaternized with diethyl sulfate, vinyl pyrrolidinone-imidazolinium methochloride copolymers and quaternized polyvinyl alcohol; zwitterionic and amphoteric polymers; structurants such as glucose, maleic acid and lactic acid, hair conditioning compounds such as phospholipids, for example lecithin and cephalin; perfume oils, dimethyl isosorbide and cyclodextrins; fiber structure improvers, in particular mono-, di- and oligosaccharides such as for example glucose, galactose, fructose, fruit sugar and lactose; colorants for coloring the agent; anti-dandruff actives such as Piroctone Olamine, Zinc Omadine and Climbazol; amino acids and oligopeptides, in particular arginine and/or serine; animal and/or vegetal based protein hydrolysates, such as for example protein hydrolysates of elastin, collagen, keratin, silk and milk albumin, or protein hydrolysates of almonds, rice, peas, potatoes and wheat, as well as in the form of their fatty acid condensation products or optionally anionically or cationically modified derivatives; vegetal oils, such as macadamia nut oil, candle nut oil, palm oil, amaranth seed oil, peach stone oil, avocado oil, olive oil, cocoa oil, rape seed oil, sesame oil, jojoba oil, soja oil, peanut oil, evening primrose oil and tea tree oil; light protective agents such as derivatized benzophenones, cinnamic acid derivatives and triazine; active substances such as pantolactone, allantoin, pyrrolidinone carboxylic acids and their salts as well as bisabolol; polyphenols, in particular hydroxycinnamic acids, 6,7-dihydroxycoumarine, hydroxybenzoic acids, catechol, tannins, leucoanthocyanidine, anthocyanidine, flavanones, flavones and flavonols; ceramides or pseudoceramides; vitamins, pro-vitamins and vitamin precursors, in particular from the groups A, $B_3$, $B_5$, $B_6$, C, E, F and H; plant extracts such as for example the extracts of aloe vera, angelica, aniseed, apricot, benzoin, bergamot, birch, stinging nettle, calmus, cassis, costic, marshmallow, oak bark, elemi, estragon, spruce needles, galbanum, geranium, ginseng, grapefruit, guaiacum wood oil, green tea, hamamelis, rest harrow, hops, coltsfoot, ginger root, iris, jasmin, camomile, cardamum, clover, burdock root, Scotch fir, kiwi, coconut, coriander, caraway, larch, lavender, lemon grass, lily, lime, linden blossom, litchi, mace, malva, almond, mango, rest harrow, melon, meristem, myrrh, neroli, olibanum, opoponax, orange, patchouli, petitgrain, pine, quendel, rooibos, rose, rosemary, horse chestnut, sandal wood, sage, field horsetail, common yarrow, celery, fir, thyme, juniper, vine leaves, hawthorn, wheat, lady's smock, ylang-ylang, cedar and lemon; fats and waxes such as fatty alcohols, beeswax, Montan wax and paraffins; swelling and penetration substances such as glycerin, propylene glycol monoethyl ether, carbonates, hydrogen carbonates, guanidines, ureas as well as primary, secondary and tertiary phosphates; opacifiers such as latex, styrene/pvp and styrene/acrylamide copolymers; pearlizers such as ethylene glycol mono- and distearate as well as PEG-3 distearate; pigments.

The person skilled in the art will select these additional substances depending on the desired properties of the ready-for-use lightening agent. With regard to further optional ingredients and their amounts used, reference is expressly made to the relevant handbooks known to the person skilled in the art, for example the monograph by K. Schräder, Grundlagen und Rezepturen der Kosmetika, 2nd edition, Hüthig Buch Verlag, Heidelberg, 1989. The additional active substances and auxiliaries are preferably incorporated in the agents according to the invention in amounts of about 0.0001 to about 10 wt %, particularly about 0.0005 to about 5 wt %, based on the total weight of the ready-for-use lightening agent.

The ready-for-use lightening agent preferably has a pH in the range about 6 to about 12. The lightening agent is particularly preferably applied in an alkaline milieu. In the context of the present invention, the pH values refer to those measured at a temperature of 22° C.

In addition, it has proved particularly preferable if the resulting ready-for-use lightening agent is formulated to be of low viscosity. Ready-for-use lightening agents, which after mixing in the first process step exhibit a viscosity of 0 to about 2000 mPas (measured at 22° C. in the Brookfield Viscosimeter type RV-T with spindle LV-1 or RV-1 and a speed of 30 rpm), have proved to be particularly preferred. According to the invention, a viscosity of 0 to about 1000 mPas, measured under the cited conditions, is particularly preferred. According to the invention, a viscosity of about 5 to about 500 mPas, in particular about 10 to about 50 mPas (measured under the cited conditions) is quite particularly preferred.

In the second process step according to the invention, the ready-for-use lightening agent is dispensed from a foam dispensing vessel and deposited onto the fibers to be lightened. It has proven advantageous to carry out the mixing of the agents (A), (B) and (C) in the first step of the inventive method directly in the foam dispensing vessel of the second process step.

It is inventively preferred if the ready-for-use lightening agent is taken up in a suitable dispenser and dispensed for each use. Fundamentally therefore, the ready-for-use lightening agent is dispensed in the form of a foam. The foam consistency of the preparation is to be very broadly understood in this context and includes any mixture of a flowable preparation and a gaseous component. In this respect, both flowable as well as essentially solid, stable foam consistencies are included in the subject matter of the invention.

According to the invention, a foam is defined as a gas-liquid mixture. A foam designates here structures of gas-filled spherical or polyhedral cells (pores) that are delimited by liquid, semiliquid or highly viscous cell walls. Inventively preferably, the gas comprised by the foam is air and/or mixtures of air and reaction gases that result when the agents (A), (B) and (C) are mixed.

The gaseous content of the foam is preferably at least about 50 vol %, preferably at least about 70 vol % and more preferably at least about 80 vol %, in each case based on the total volume of the ready for use agent.

If the volume concentration of the gases that form the foam is less than about 74% for a homodisperse distribution, then the gas bubbles are spherical due to the action of the surface tension to minimize the surface area. Above the limit of the closest spherical packing, the bubbles are deformed to polyhedral lamellae that are limited by ca. 4 to 600 nm thin skins. The cell walls, connected over so called Plateau borders, form a coherent framework. The foam lamellae are stressed between the cell walls (closed-cell foam). It the foam lamellae are destroyed or they flow back into the cell walls at the end of the foam formation, then an open-cell foam is obtained.

Inventively particularly suitable foams possess a gas-liquid ratio of about 5 to about 50 mL/g, preferably about 10 to about 40 mL/g and especially about 15 to about 35 mL/g. This gas-liquid ration is determined for example in that after the end of the mixing process at room temperature and a rest period of 1 minute, the volume of the foam is measured, for example with a measuring cylinder, for a known weight of the agents (A), (B) and (C). Alternatively, a defined volume, for example by dispensing into a measuring cylinder, can be removed and its weight measured by weighing.

Basically a foam dispenser vessel according to the invention includes at least one reservoir to receive at least one component of the lightening agent and an application device to dispense the lightening agent in the form of foam. Here the reservoir is especially designed as a tube-shaped or bottle-shaped container, whereas the application device closes this container that is open on one side. The actual dispensing of the preparation is preferably effected by means of a suitable pressure source that is integrated into the dispenser, in particular in the reservoir, or by means of a manual pressure build-up initiated by the actual user of the lightening agent.

As an example of inventive dispensers with an integrated pressure source, one may mention pressure vessels that usually have either a suitable pressure accumulator inside the container, e.g. mechanical, or they comprise a propellant, and in this way place the inside of the container under pressure. These types of pressure vessels are usually equipped with suitable valve devices for dispensing the preparation located inside the pressure vessel when the corresponding valve is actuated. Such pressure vessels in conjunction with gaseous and/or liquid propellants are known mainly in the form of aerosol dispensers for the most varied cosmetic applications, e.g. hair styling sprays, hair dye preparations, deodorant sprays, shaving foam/gels, etc.

Alternatively, manually actuated dispensers can also be used according to the invention; they rely solely on the force exerted by the user in order to dispense a foamed preparation. These types have the advantage that an additional pressure source, e.g. propellant, is not required; this is desirable—principally on the grounds of cost and sustainability. These foam dispensers actuated by manual force provide not only for the delivery of the lightening agent out of the reservoir to the dispensing outlet but at the same time also for an appropriate foaming of the lightening agent. During this foaming or foam formation, the lightening agent is basically mixed with a gaseous component, especially air. Specifically, a foaming device that does this is provided for this purpose.

According to a first variant of a manually actuatable dispenser, it is designed as a shakable dispenser, having at least one reservoir for receiving the lightening agent, and an associated dispensing device for dispensing the foamed lightening agent. In this regard the dispensing device is in particular detachably connected to the reservoir. The actual foam formation occurs inside the shakable dispenser by shaking the lightening agent inside the reservoir. The shakable dispenser in conjunction with the appropriate movement of the dispenser thereby forms the above cited foaming device. Subsequent to this type of foaming, the foamed lightening agent can then be dispensed by means of the dispensing device.

Another reasonable dispenser variant is provided by the development as a squash- or squeeze-foam dispenser. A squeeze-foam dispenser possesses, besides the at least one reservoir for receiving the lightening agent, an appropriate application device, inside which occurs the foaming as well as the subsequent delivery of the lightening agent. The lightening agent is actually delivered from the reservoir by means of a force exerted onto the flexible wall of the reservoir. Here, the reversible deformation of the reservoir wall creates a pressure increase inside the reservoir, resulting in the lightening agent being forced out of the reservoir. For this to happen the reservoir wall has to be designed to be sufficiently flexible or reversibly deformable. This is ensured by a design thickness of the reservoir wall appropriate to the required application, in conjunction with a suitable choice of material for the reservoir wall. The reservoir wall of a suitable squeeze foam dispenser is preferably made of a polyolefin, such as for example polypropylene (PP), high density polyethylene (HDPE), medium density polyethylene (MDPE), low density polyethylene (LDPE), linear low density polyethylene (LLDPE). Among these, polypropylene (PP) is preferred.

The application device of such a squeeze-foam dispenser also includes a suitable foaming device for foaming the lightening agent. The foaming device is capable of blending a quantity of the preparation with a quantity of the gas in the appropriate blend ratio in order to generate the desired foam consistency of the lightening agent. For this, a flow of the preparation and a flow of the gas are drawn together into a mixing chamber of the foaming device and blended together by fluid dynamic turbulence. Air is particularly preferably used as the gaseous component for the foam formation and is drawn in either directly from the reservoir or from the surroundings.

The basic functionality of this type of squeeze foam dispenser is also described in the documents WO 2007/086730 A2/A3 and EP 1237660 B1. A squeeze foam dispenser according to the invention can also be correspondingly designed from these patent documents.

In particular, the inventive squeeze foam dispenser according to the disclosure of EP 1 237 660 B1 can be designed such that it is possible to use the dispenser in the essentially upright position as well as in the overhead position.

Similarly, the dispenser can also be designed as a pump foam dispenser with at least one reservoir for receiving the lightening agent as well as an application device, wherein in this case the application device possesses a pump device for delivering both the lightening agent and the gaseous component, preferably air, and moreover includes an appropriate foaming device. Details of the mode of operation and the structural design of this type of pump foam dispenser are also found inter alia in the patent documents WO 2007/083206 A1 or WO 2007/091882 A1. In particular, the inventive pump foam dispenser can be designed according to the disclosure of these cited documents.

When using the cited dispensing variants in connection with multi-component agents, it must be ensured that the individual components are stored separately until the actual application of the preparation. The lightening agent is inventively applied with one of the above described dispenser variants having only one reservoir and one application device. For this, the reservoir is designed in such a way that it can be opened and reclosed. Ideally, the reservoir is closed by means of the application device, wherein the application device is detachably connected to the reservoir, for example by a screw- or snap-connection. This opens up the possibility of pre-filling the reservoir during manufacture with one component of the lightening agent and to only add additional components of the lightening agent into the reservoir shortly before actually using the lightening agent. In this connection, the additional components are inside suitable separate containers in the form of a kit and are added to the total lightening agent and are mixed in the reservoir by the user immediately prior to using the lightening agent.

In all the listed dispenser variants the individual components of the lightening agent can be more easily or better mixed inside the respective application device by using suitable additional mixing devices, e.g. a static mixer (as is also described in WO 2005/102539 A1) or a porous insert element. These types of mixing devices can be advantageously located at a suitable position inside a flow channel for the lightening agent in the application device.

Moreover in addition, one or more porous insert elements can be incorporated in order to positively influence the attainable foam consistency inside the foaming device. Such porous insert elements are for example spongy or net-like in structure and are positioned inside the foaming device at suitable places in the flow channel for the lightening agent, for example directly upstream of the delivery outlet of the dispenser. This allows the lightening agent to flow through the porous insert element and as a result of fluid dynamic turbulence affords a finer and more homogenous foam consistency. The foam consistency can therefore be directly influenced depending on the particular design of the porous insert element. When using a net-like insert element, it has proven expedient to preferably design the net-like insert element with openings of about 50 to about 220 mesh (mesh=number of openings per inch), particularly preferably about 90 to about 200 mesh, quite particularly preferably about 125 to about 175 mesh. When using a plurality of net-like insert elements it is also possible to use insert elements having different openings. In this case, the first upstream-positioned net like insert element preferably has openings of about 50 to about 220 mesh (mesh=number of openings per inch), particularly preferably about 90 to about 200 mesh, quite particularly preferably about 125 to about 175 mesh. The second downstream-positioned net preferably has openings of about 160 to about 280 mesh, particularly about 175 to about 245 mesh and quite particularly preferably about 180 to about 220 mesh. Finally, the number of the porous insert elements used as well as their specific openings or their porosity characteristics can be designed accordingly depending on the relevant type of application.

The ready-for-use lightening agent is dispersed onto the fibers, especially human hair, by the user, preferably by hand, optionally also with a technical auxiliary, such as a comb, brush or paintbrush. In this regard the ready-for-use lightening agent can be immediately applied as the discharged foam onto the hair roots and then dispersed onto the fibers with the hands or with a mechanical auxiliary. However, it is also conceivable to initially deposit the foam onto a mechanical auxiliary, such as a comb, and then with its help disperse the foam onto the fibers. Independently of how the foam is applied, it can be inventively preferred to subsequently massage the foam into the hair.

In the third process step of the inventive method of the first subject matter of the invention, the lightening agent remains on the fibers being lightened for a contact time of about 1 to about 60 minutes, preferably about 5 to about 45 minutes.

The application temperatures of the lightening agent can range between about 15 and about 40° C. An external heat source can also be optionally employed to supply heat. The lightening is particularly preferably supported by physical measures. Inventive methods, in which the application is supported by the action of heat, IR and/or UV radiation during the contact time, are preferred.

Finally, in the fourth process step the residual lightening agent is removed from the fibers by rinsing out the fibers being lightened.

Depending on the surfactant content of the ready-for-use lightening agent, the rinsing can be effected with water or a surfactant-containing agent, such as for example a shampoo.

Depending on the users' wishes, still more steps can be added to the method, such as for example additional fiber-care steps with a conditioner or shaping steps to style the hair in the case of application on human hair.

A second inventive subject matter of the present application is an agent for lightening keratinic fibers which is produced by blending three separately packaged preparations, and which is characterized in that one of the preparations represents an agent (A), that one of the preparations represents an agent (B) and that one of the preparations represents an agent (C) according to the first subject matter of the invention.

Accordingly, a preferred embodiment of the second subject matter of the invention is characterized in that the ready for use lightening agent is in the form of a foam.

It can be preferred to store the agents (A), (B) and (C) separately from each other. Advantageously, however, the agents are provided to the user in one overpack.

A third subject matter of the present invention is a kit for lightening keratinic fibers, characterized in that it has at least three separately packaged components, wherein the first component comprises an agent (A), comprising at least one alkalizer, the second component comprises an agent (B), comprising at least one oxidizing agent, and the third component comprises an agent (C), comprising at least one peroxo salt.

The separately packaged agents or components are provided in physically separate containers. The term "container" herein designates a holder, independently of its shape, material or closure, which is capable of containing substances or mixtures of substances. Consequently, the term "container" includes, but is not limited to the interior of a tube, of a pouch or bag, of a canister, of a can, of a pan, of a bottle, of a glass or of a packet, of a carton, of a box, of an envelope or of another container. The components of the preparations can be comprised in a single container that possesses a plurality of compartments to receive the preparations; however, it is also possible and optionally preferred to allocate them to different containers.

For the blending and discharging as a foam the kit of parts additionally comprises at least one foam dispensing vessel that, as already mentioned, can also be employed as a reservoir for one of the agents (A), (B) or (C).

Accordingly, one embodiment of the third subject matter of the invention is characterized in that the kit of parts additionally comprises a dispensing vessel that is suitable for discharging the ready-for-use mixture of the agents (A) (B) and (C) in the form of a foam.

With reference to further preferred embodiments of the kit according to the invention, the statement made concerning the method and agents according to the invention applies mutatis mutandis.

EXAMPLES

The following formulations were produced: Unless otherwise stated, the quantities are each understood to be in weight percent.

1. Blonding Cream (Agent A)

| Raw material | A |
| --- | --- |
| Plantacare 818 UP | 25.00 |
| Genagen KB | 30.00 |
| Cremophor CO 60 | 3.00 |
| Tetrasodium EDTA | 0.20 |
| Sodium sulfite | 0.10 |
| Ascorbic acid | 0.05 |
| L-serine | 1.00 |
| Monoethanolamine | 8.00 |
| Eau Vitale d'algue bleue | 2.00 |
| Merquat 281 | 3.00 |
| Perfume | qs |
| Water | ad 100 |

2. Developer Preparations (Agent B)

| Raw material | B |
| --- | --- |
| Dipicolinic acid | 0.10 |
| Disodium pyrophosphate | 0.03 |
| Aculyn 33A | 2.50 |
| Texapon NSO | 2.00 |
| Sodium hydroxide (aqueous 45% conc.) | 0.73 |
| Turpinal SL | 1.50 |
| Hydrogen peroxide (aqueous, 50% conc.) | 15.20 |
| Water | ad 100 |

3. Blonding Powder (Agent C)

| Raw material | C1 | C2 |
| --- | --- | --- |
| Sodium persulfate | 100 | — |
| Ammonium persulfate, 98% + Silica, 2% | — | 100 |

4. Index of the Utilized Commercial Products

| | |
| --- | --- |
| Aculyn 33A | ca. 28% solids in water; INCI name: Acrylates Copolymer |
| Cremophor CO60 | INCI name: PEG-60 Hydrogenated Castor Oil (BASF) |
| Merquat 281 | ca. 40% active substance INCI name: Aqua (Water), Polyquaternium-22 (Cognis) |
| Eau Vitale d'algue bleue | ca. 0.1-0.99 (wt % active substance) INCI name: Aqua (Water), Plankton Extract, Penoxyethanol (Soliance) |
| Plantacare 818UP | ca. 51-53% active substance) INCI name: Coco-Glucoside, Aqua (Water) (Cognis) |
| Texapon NSO | ca. 27.5% active substance INCI name: Sodium Laureth Sulfate (Cognis) |
| Turpinal SL | ca. 58-61% active substance; INCI name: Etidronic Acid, Aqua (Water) (Solutia) |

5. Lightening 5.1 Application with a Squeeze Foam Dispenser 35 g of the Agent B were placed in a squeeze foam dispenser. Immediately prior to application 35 g of the Agent B and 10 g of the Agent (C1) or (C2) were carefully added such that no foam formation occurred. The squeeze bottle was then carefully turned upside down and back several times, so as to effect a thorough mixing of the components without extensive foaming. The foam was discharged directly onto the hair line of a subject by pressing the squeeze foam dispenser, the hair was then wetted and finally the foam was evenly distributed into the fibers with a comb. After a contact time of 45 minutes at room temperature the hair was thoroughly rinsed with water, shampooed and dried with a hair-dryer.

5.2 Application with Pump Foam Dispensers 35 g of the Agent B was placed in a pump foam dispenser. Immediately prior to application 35 g of the Agent B and 10 g of the Agent (C1) or (C2) were carefully added such that no foam formation occurred. The pump dispenser was then carefully turned upside down and back several times, so as to effect a thorough mixing of the components without extensive foaming. Using the pump head, the foam was initially discharged into the palm of the hand and then applied to the hair line and the hair; finally the foam was evenly distributed into the fibers with a comb. After a contact time of 45 minutes at room temperature the hair was thoroughly rinsed with water, shampooed and dried with a hair-dryer.

The invention claimed is:

1. A method for lightening keratinic fibers comprising the steps of:

i. preparing a ready for use lightening agent immediately before use by combining:

an agent (A), comprising an alkalizer and a zwitterionic surfactant of the Formula (I),

in which

R stands for a saturated or unsaturated $C_{10}$-$C_{20}$ alkyl chain, and

R1 and R2 each stand independently of one another for a $C_1$-$C_4$ alkyl group or a $C_2$-$C_4$ hydroxyalkyl group, an agent (B), comprising an oxidizing agent, and an agent (C), comprising a peroxy salt, and subsequently blending, ii. dispensing the ready for use lightening agent out of a pump foam dispensing vessel having at least one reservoir configured to receive the lightening agent and spreading the ready for use lightening agent onto the keratinic fibers, iii. maintaining the ready for use lightening agent on the keratinic fibers for a period of about 1 to about 60 minutes, and iv. washing out of the keratinic fibers.

2. The method according to claim 1, characterized in that the agent (A) comprises an alkanolamine as the alkalizer.

3. The agent according to claim 1, characterized in that the agent (A) comprises one or more zwitterionic surfactants of the Formula (I) in a total weight fraction of at least about 2.5 wt %, based on the total weight of the ready for use lightening agent.

4. The method according to claim 1, characterized in that the agent (A) additionally comprises a non-ionic surfactant chosen from the group comprising alkyl polyglucosides, alkenyl polyglucosides, and ethoxylated, non-ionic surfactants containing at least 30 ethylene oxide units.

5. The method according to claim 1, characterized in that the agent (C) comprises sodium persulfate and/or ammonium persulfate as the peroxo salt.

6. The agent according to claim 1, characterized in that the ready for use lightening agent has a total surfactant content of at least about 10 wt %, based on the total weight of the ready for use lightening agent.

7. A lightening agent for keratinic fibers comprising:
an agent (A), comprising an alkalizer and a zwitterionic surfactant of the Formula (I),

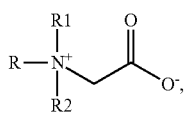
(I)

in which
R stands for a saturated or unsaturated $C_{10}$-$C_{20}$ alkyl chain, and
R1 and R2 each stand independently of one another for a $C_1$-$C_4$ alkyl group or a $C_2$-$C_4$ hydroxyalkyl group,
an agent (B), comprising an oxidizing agent, and
an agent (C), comprising a peroxy salt,
wherein each agent is a separately packaged preparation, and agents (A), (B), and (C) are adapted to be blended together to obtain the lightening agent,
wherein the lightening agent is in the form of a foam that is formulated to be dispensed from a pump foam dispenser having at least one reservoir for receiving the lightening agent.

8. A kit of parts for lightening keratinic fibers, comprising three separately packaged components, wherein the first component comprises an agent (A), comprising an alkalizer and a zwitterionic surfactant of the Formula (I),

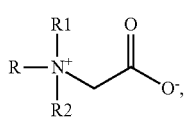
(I)

in which
R stands for a saturated or unsaturated $C_{10}$-$C_{20}$ alkyl chain, and
R1 and R2 each stand independently of one another for a $C_1$-$C_4$ alkyl group or a $C_2$-$C_4$ hydroxyalkyl group,
the second component comprises an agent (B), comprising an oxidizing agent, and,
the third component comprises an agent (C), comprising a peroxo salt, and
a dispensing vessel suitable for discharging a mixture of the agents (A) (B) and (C) in the form of a foam.

9. The agent according to claim 1, characterized in that the agent (A) comprises one or more zwitterionic surfactants of the Formula (I) in a total weight fraction of at least 3 wt %, based on the total weight of the ready-for-use agent.

10. The agent according to claim 9, characterized in that the agent (A) comprises one or more zwitterionic surfactants of the Formula (I) in a total weight fraction of at least 4 wt %, based on the total weight of the ready-for-use agent.

11. The agent according to claim 6, characterized in that the ready for use lightening agent has a total surfactant content of at least 12 wt %, based on the total weight of the ready-for-use lightening agent.

12. The method according to claim 7, characterized in that the agent (A) comprises an alkanolamine as the alkalizer.

13. The agent according to claim 7, characterized in that the one or more zwitterionic surfactants of the Formula (I) of agent (A) comprises at least about 2.5 wt %, based on the total weight of the ready for use lightening agent.

14. The method according to claim 7, characterized in that the agent (A) additionally comprises a non-ionic surfactant chosen from the group comprising alkyl polyglucosides, alkenyl polyglucosides, and ethoxylated, non-ionic surfactants containing at least 30 ethylene oxide units.

15. The method according to claim 7, characterized in that the agent (C) comprises sodium persulfate and/or ammonium persulfate as the peroxo salt.

16. The agent according to claim 7, characterized in that the ready for use lightening agent has a total surfactant content of at least about 10 wt %, based on the total weight of the ready for use lightening agent.

* * * * *